June 7, 1955 E. S. BOERNER Plant Pat. 1,396
ROSE PLANT
Filed Oct. 11, 1954
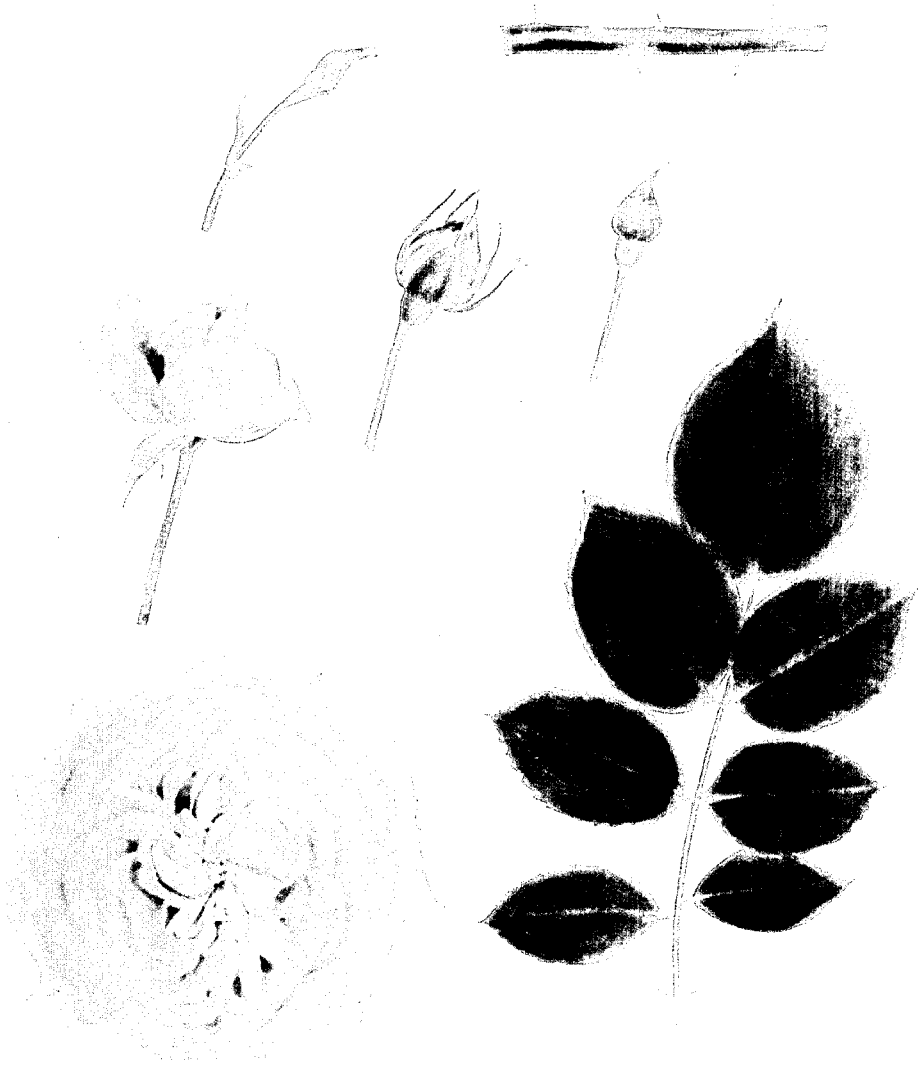
Inventor.
E. S. Boerner
By: Robb & Robb
Attorneys.

United States Patent Office

Plant Pat. 1,396
Patented June 7, 1955

1,396

ROSE PLANT

Eugene S. Boerner, Newark, N. Y., assignor to Jackson & Perkins Company, Newark, N. Y., a corporation of New York Application October 11, 1954, Serial No. 461,701

1 Claim. (Cl. 47—61)

The present invention relates to a new and distinct variety of rose plant of the large-flowered polyantha class, which was originated by me by crossing an unnamed and unpatented seedling of "Goldilocks" (Plant Patent No. 672) × "Floradora" (unpatented) with another unnamed and unpatented Floribunda seedling derived from unnamed and unpatented parents.

The primary objective of this cross was to obtain a new variety of rose having a compact plant growth suitable for greenhouse forcing, and which bears clusters of flowers of long-lasting quality and of a distinctive color which is maintained until all of the flowers of the cluster are open, as well as having a substantially continuous succession of new flowers.

This objective was fully achieved by the breeding noted above, as evidenced by the fact that my new variety is particularly characterized by the following outstanding features:

(1) A compact bush form of the plant which forces very easily in winter and comes into bloom with a fine display of flowers;

(2) The flowers are usually borne in clusters and are long-lasting both on the plant and as cut flowers;

(3) The distinctive color of the flowers which is definitely different from that of any similar forcing rose of the same size and shape, said color being generally characterized as Scarlet Red, lightly overcast with Scarlet; and (4) The continuous blooming habit of the flowers, combined with retention of the individual cluster flower color until all of the flowers of the cluster are open.

The foregoing characteristics definitely distinguish my new variety from its parents, as well as from all other varieties of the same class of which I am aware, and asexual reproduction of the new variety by budding, as performed at Newark, New York, and at Pleasanton, California, shows that these characteristics and distinctions come true to form and are established and transmitted through succeeding propagations.

The accompanying drawing shows typical specimens of the foilage, stems and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Goldilocks" × "Floradora."

*Pollen parent.*—An unnamed floribunda seedling of unnamed parents.

Classification:

*Botanic.*—Large-flowered Polyantha.

*Commercial.*—Floribunda.

FLOWER (Observations made in a greenhouse at Newark, New York, in the early morning, in the early part of the month of April.)

Blooming habit: Excellent for growing as a plant for winter forcing. Recurrent—continuous.

Bud:

*Size.*—Medium.

*Form.*—Globular; is not affected by wet or hot weather.

*Color.*—When sepals first divide—Carmine, Plate 1. When petals begins to unfurl—Spectrum Red, Plate 1. When half blown: Inside of petals—Scarlet Red, Plate 1, lightly overcast with Spectrum Red, Plate 1; reverse of petals—Spectrum Red, Plate 1, lightly overcast with Scarlet Red, Plate 1.

*Sepals.*—Slightly branched; curl back when petals begin to unfurl. Color: Inside—Absinthe Green, Plate 31; outside—Jade Green, Plate 31.

*Calyx.*—Color—Jade Green, Plate 31. Shape—pear. Size—small. Aspect—smooth. Odor when rubbed—none.

*Peduncle.* — Length — medium. Aspect—smooth. Strength—erect; slender. Color—Parrot Green, Plate 6.

*Opening.*—Opens up well; is not affected by adverse weather conditions.

Bloom:

*Size.*—Medium. Average size when fully expanded—3 inches.

*Borne.*—Several together and in rounded clusters.

*Stems.*—Medium length; normal strength.

*Form (when first open).*—Cupped. Permanence—flattens.

*Petalage.*—Very double (many petals and stamens hidden). Number of petals under normal conditions—from 50 to 55.

*Color.*—Center of flower—Scarlet Red, Plate 1, lightly overcast with Scarlet, Plate 1. Outer petals—Scarlet Red, Plate 1, lightly overcast with Begonia Rose, Plate 1. Base of petals (aiglet)—Citron Yellow, Plate 16. Inside of petals—Scarlet Red, Plate 1, lightly overcast with Scarlet, Plate 1. Reverse of petals—Rose Red, Plate 12, lightly overcast with Scarlet Red, Plate 1. General tonality from a distance—Scarlet Red, Plate 1, light overcast with Scarlet, Plate 1.

*Discoloration.*—General tonality at end of first day—Scarlet Red, Plate 1, lightly overcast with Scarlet, Plate 1. Second day—Scarlet Red, Plate 1, lightly overcast with Scarlet, Plate 1. Third day—Scarlet, Plate 1, lightly overcast with Scarlet Red, Plate 1.

Petals:

*Texture.*—Leathery; is not affected by wet or hot weather.

*Appearance.*—Inside—shiny; outside—satiny.

*Form.*—Oval; slightly notched.

*Arrangement.* — Imbricated (regularly arranged shingle-like).

*Petaloids in center.*—Few; small.

*Persistence.*—Drop off cleanly.

*Fragrance.*—Moderate. Nature—tea (average hybrid tea scent).

*Lasting quality.*—On the plant—long; as cut flower—long.

GENITAL ORGANS

Stamen, anthers: Small; few; regularly arranged around styles. Color—Yellow Ochre, Plate 15.

Staments, filaments (threads): Short. Color—Light Greenish Yellow, Plate 5.
Pollen: Color—Warm Buff, Plate 15.
Styles: Loosely separated; uneven length; short; thin.
Stigmas: Color—Primrose Yellow, Plate 30.
Ovaries: All enclosed in calyx.
Hips: None.
Seeds: None.

PLANT

Form: Bush.
Growth: Vigorous; compact.
Foliage: 5 to 7 leaflets.
*Size.*—Medium.
*Quantity.*—Abundant.
*Color.*—New foliage: Upper side—Light Bice Green, Plate 17; under side—Courge Green, Plate 17. Old foliage: Upper side—Elm Green, Plate 17; under side—Light Elm Green, Plate 17.
*Shape.*—Oval pointed.
*Texture.*—Upper side—glossy; under side—smooth.
*Ribs and veins.*—Ordinary.
*Edge.*—Serrated (saw-toothed).
*Serration.*—Both double and single; small.
*Leaf stem.*—Color—Absinthe Green, Plate 31. Under side—prickles.
*Stipules.*—Short; bearded.
Wood:
*New wood.*—Color—Oil Green, Plate 5. Bark—smooth.

*Old wood.*—Color—Cress Green, Plate 31. Bark—smooth.
Thorns:
*Thorns.*—Quantity: On main stalks from base—ordinary; on laterals from stalk—ordinary. Form—narrow base; medium length; some straight and some hooked downward. Color (when young)—Deep Colonial Buff, Plate 30. Position—irregular.
*Prickles.*—Quantity: On main stalks—none; on laterals—none.
*Short needles.*—Quantity: On main stalks—none; on laterals—none.

I claim:

A new and distinct variety of rose plant of the large-flowered polyantha class, substantially as herein shown and described, characterized particularly as to novelty by its compact plant growth and suitability for greenhouse forcing, by its substantially continuous formation and excellent display of flowers, by the cluster habit of its flowers, by the distinctive Scarlet Red, lightly overcast with Scarlet general color tonality of its flowers, and by the retention of the individual flower color until all of the flowers of the cluster are open.

No references cited.